United States Patent
McDonald et al.

(10) Patent No.: US 11,672,677 B2
(45) Date of Patent: *Jun. 13, 2023

(54) MANAGEMENT OF WIRELESS TRANSMISSION RATE OF CONTROL SIGNALS FOR POWER ASSISTIVE DEVICES

(71) Applicant: Liberating Technologies, Inc., Holliston, MA (US)

(72) Inventors: Benjamin Edward McDonald, Holliston, MA (US); Todd Richard Farrell, Waltham, MA (US); Edward Clancy, Framingham, MA (US); Jianan Li, Worcester, MA (US); Xinming Huang, Natick, MA (US)

(73) Assignee: LIBERATING TECHNOLOGIES, INC., Holliston, MA (US)

( * ) Notice: Subject to any disclaimer, the term of this patent is extended or adjusted under 35 U.S.C. 154(b) by 9 days.

This patent is subject to a terminal disclaimer.

(21) Appl. No.: 17/507,881

(22) Filed: Oct. 22, 2021

(65) Prior Publication Data
US 2022/0039973 A1    Feb. 10, 2022

Related U.S. Application Data

(62) Division of application No. 16/698,623, filed on Nov. 27, 2019, now Pat. No. 11,154,408.
(Continued)

(51) Int. Cl.
*G09B 21/00* (2006.01)
*A61F 2/72* (2006.01)
(Continued)

(52) U.S. Cl.
CPC .............. *A61F 2/72* (2013.01); *A61H 1/0237* (2013.01); *A61H 1/0274* (2013.01); *A61H 3/00* (2013.01);
(Continued)

(58) Field of Classification Search
CPC .. A61F 2/72; A61F 2/582; A61F 2/585; A61F 2/588; A61F 2/64; A61F 2/6607;
(Continued)

(56) References Cited

U.S. PATENT DOCUMENTS

| 7,162,288 B2 | 1/2007 | Nordstrom et al. |
| 9,560,994 B2 | 2/2017 | McCutcheon et al. |

(Continued)

OTHER PUBLICATIONS

Benatti, S. et al. "A Prosthetic Hand Body Area Controller Based on Efficient Pattern Recognition Control Strategies" Sensors 2017, 17, 869.

(Continued)

*Primary Examiner* — Tanmay K Shah
(74) *Attorney, Agent, or Firm* — Dinsmore & Shohl LLP

(57) ABSTRACT

A system and method for transmission of a signal for a powered assistive device has a sensor node with a wireless transmitter adapted for digitally transmitting a transmitted signal, the sensor node adapted for receiving and monitoring a sensor signal from a sensor attached to a user, and a master node with a controller and a wireless receiver for receiving the transmitted signal from the wireless transmitter. The master node processes the transmitted signal and communicates a control signal to the powered assistive device. The wireless transmitter transmits the transmitted signal at a first rate when the wireless transmitter adapted to transmit the transmitted signal at a first rate when the sensor signal is indicative of the rest state and to transmit the transmitted signal at a second rate when the sensor signal is indicative of the active state, the second rate being greater than the first rate.

11 Claims, 9 Drawing Sheets

Related U.S. Application Data

(60) Provisional application No. 62/772,255, filed on Nov. 28, 2018.

(51) Int. Cl.
*H04Q 9/00* (2006.01)
*A61H 3/00* (2006.01)
*A61H 1/02* (2006.01)
*G08C 17/02* (2006.01)
*A61F 2/58* (2006.01)
*A61F 2/70* (2006.01)
*A61F 2/64* (2006.01)
*A61F 2/66* (2006.01)

(52) U.S. Cl.
CPC .............. *G08C 17/02* (2013.01); *H04Q 9/00* (2013.01); *A61F 2/582* (2013.01); *A61F 2/585* (2013.01); *A61F 2/588* (2013.01); *A61F 2/64* (2013.01); *A61F 2/6607* (2013.01); *A61F 2002/705* (2013.01); *A61H 2201/5061* (2013.01); *A61H 2201/5082* (2013.01); *A61H 2201/5084* (2013.01); *A61H 2201/5097* (2013.01); *A61H 2230/605* (2013.01); *G08C 2201/12* (2013.01); *H04Q 2209/43* (2013.01); *H04Q 2209/826* (2013.01); *H04Q 2209/883* (2013.01)

(58) Field of Classification Search
CPC ............ A61F 2002/705; A61H 1/0237; A61H 1/0274; A61H 3/00; A61H 2201/5061; A61H 2201/5082; A61H 2201/5084; A61H 2201/5097; A61H 2230/605; A61H 1/024; A61H 1/0266; A61H 1/0285; A61H 1/0277; A61H 2201/5007; G08C 17/02; G08C 2201/12; H04Q 9/00; H04Q 2209/43; H04Q 2209/826; H04Q 2209/883
USPC ........................................................ 340/4.1
See application file for complete search history.

(56) References Cited

U.S. PATENT DOCUMENTS

| | | |
|---|---|---|
| 11,154,408 B2 * | 10/2021 | McDonald ............... A61H 3/00 |
| 2007/0244398 A1 | 10/2007 | Lo et al. |
| 2010/0305414 A1 | 12/2010 | Koo et al. |
| 2011/0288448 A1 | 11/2011 | Sanders et al. |
| 2014/0249397 A1 | 9/2014 | Lake et al. |
| 2014/0320307 A1 | 10/2014 | Matsuno et al. |
| 2015/0066153 A1 | 3/2015 | Palmer, III et al. |
| 2015/0105664 A1 | 4/2015 | Imamura |
| 2015/0362331 A1 | 12/2015 | Sanchez et al. |
| 2015/0374310 A1 | 12/2015 | Lee |
| 2016/0361014 A1 | 12/2016 | Kane et al. |
| 2017/0258585 A1 | 9/2017 | Marquez et al. |
| 2018/0092536 A1 | 4/2018 | Sandler et al. |

OTHER PUBLICATIONS

Ciancio, A. L. et al. "Control of Prosthetic Hands via the Peripheral Nervous System", Frontiers in Neuroscience, Apr. 1, 2016, vol. 10, Article 116.

Cloutier, A. et al. "Control of Hand Prostheses—A Literature Review" Proceedings of the ASME 2013 International Design Engineering Technical Conferences and Computers and Information in Engineering Conference, IDETC/CIE Aug. 4-7, 2013, 2013, Portland, Oregon, USA, DETC2013-13349.

Kakoty, N. M. et al. "Bio-Signals Controlled Prosthetic Hand" Tezpur University, School of Engineering, Tezpur, India.

Sadikoglu, F. et al. "Electromyogram (EMG) signal detection, classification of EMG signals and diagnosis of neuropathy muscle disease" 9th International Conference on Theory and Application of Soft Computing, Computing with Words and Perception, ICSCCW 2017, Aug. 24-25, 2017, Budapest, Hungary; Procedia Computer Science 120 (2017) 422-429.

Sudarsan, S. et al. "Design and Development of EMG Controlled Prosthetics Limb" International Conference on Modeling and Optimization and Computing; Procedia Engineering 38 (2012), 3547-3551.

* cited by examiner

MANAGEMENT OF WIRELESS TRANSMISSION RATE OF CONTROL SIGNALS FOR POWER ASSISTIVE DEVICES

REFERENCE TO RELATED APPLICATIONS

This application is a division of U.S. application Ser. No. 16/698,623, filed Nov. 27, 2019, which claims the benefit of U.S. Provisional Application Ser. No. 62/772,255, filed Nov. 28, 2018, the entire contents of each of which are incorporated herein by reference.

GOVERNMENT SUPPORT

This invention was made with government support under contract number W81WH18C0111 awarded by the USA Med Research ACQ Activity of the Department of Defense. The government has certain rights in the invention.

FIELD OF THE INVENTION

The present invention relates to management of the wireless transmission rate of control signals for powered assistive devices, such as powered orthotics, powered prosthetics and powered exoskeletons, based on signals from a user.

BACKGROUND OF THE INVENTION

Powered assistive devices, such as powered orthotics, powered prosthetics and powered exoskeletons, are not actuated for much of the time during which they are worn or used. For example, the devices may not require any action when the user is resting or generally inactive. However, data is generally transmitted on a regular basis from the sensors to the powered assistive device, regardless of the active/non-active state of the powered assistive device. This results in an increased power requirement for the wireless transmissions system and the powered assistive device. As the system needs to be recharged for continued usage, increased power requirement limits the duration before which a device needs recharging. Therefore, it would be desirable to overcome the limitations of existing terminal devices and to provide a better solution.

SUMMARY OF THE INVENTION

Powered assistive devices, such as powered orthotics, powered prosthetics and powered exoskeletons, enhance the function and lifestyle of persons with limb loss or impairment. These powered assistive devices may be artificial devices that replace and/or assist a function of a missing or impaired body part, which may be lost or impaired through trauma, disease, or a condition present at birth (e.g. congenital disorder). Such powered assistive devices are intended to restore the normal functions of the missing body part. In certain embodiments, a "powered assistive device" is defined as being a powered prosthetic/orthotic device or a powered exoskeleton. In further embodiments, a powered assistive device may be more broadly defined as any powered device controlled by user sensors communicating wirelessly with the device. A further example could be a powered wheelchair.

The present invention provides a system and method for management of wireless transmission (MWT) rate for control of a powered assistive device based on a signal from a user. As noted above, the powered assistive device according to certain embodiments includes a powered prosthetic, orthotic or exoskeleton device. The signal may be biological or movement signal such as an electromyographic (EMG) signal, body movement via IMU, a switch or a button, as well as signals from other sensor types. This signal is measured by a sensor. The sensor may be an EMG electrode attached to the user's skin, an inertial measurement unit (IMU), or any other type of sensor suitable for a specific application. The EMG signal (electrical impulses) is generated by the muscles of a user's body, e.g. the user's residual limb, muscle or brain. For example, a myoelectric prosthesis uses the electrical signals, generated every time a muscle contracts, as control input information. These signals can be captured from voluntarily contracted muscles by electrodes applied on the skin to control the movements of the prosthesis, such as elbow flexion/extension, wrist supination/pronation (rotation) or opening/closing of the fingers. A prosthesis of this type utilizes the residual neuromuscular system of the human body to control the functions of an electric powered prosthetic/orthotic/exoskeletal hand, wrist, elbow, foot or other joint. In the following discussion, EMG signals are used as an exemplary signal for obtaining information from the user. It should be noted that any other form of signal, e.g. EMG signal, body movement via IMU, a switch, a button or any other signal, that indicates the user's desire to keep a muscle or powered assistive device in an active or resting state may be used. These signals may be indicative of user's desire to move a muscle or part of the body.

A powered assistive device is generally not always actuated when it is worn or used by a user; for example, when the relevant limb of the user is inactive, and when the user is resting or not actively using their powered assistive device. The powered assistive device may be actuated by a wireless electromyographic (EMG) signal of the user. However, the EMG signal is not zero-valued when a muscle is at rest. Rather, a small noise signal exists due to residual bioelectrical activity within the body, electrode-skin interface noise, power-line interference and noise in the EMG analog front end. If left unaccounted for, an EMG-controlled device would "drift" from its intended rest position due to inadvertent, low-intensity action attributed to this noise. Also, transmitting a control signal based on this low level signal uses power when no activity is desired from the powered assistive device. In some embodiments, the rate of change of the sensor signal determines the active/inactive state of the muscle.

Transmitting information continuously between the sensors and the powered assistive device increases power consumption. In order to conserve power in some embodiments, the signal is transmitted at a first rate when the sensor/EMG signal is at or below a threshold level and the signal is transmitted at a second rate when the sensor/EMG signal is above the threshold level. Threshold level/value is defined as the value of the EMG signal when the user is not using the powered assistive device, does not want to use the powered assistive device and/or wants to keep the powered assistive device inactive/minimally active. In other words, the EMG signal at or below the threshold value defines the muscle rest state of the user. If the user desires to operate the powered assistive device, the user's body generates the EMG signal that is above the threshold value. Thus, the EMG signal above the threshold value reveals that the user wants to use/activate the powered assistive device. In a non-limiting example, if the threshold value of the EMG signal indicates that the user desires to operate the powered assistive device, then all the EMG signal data is transmitted in a raw or processed form. However, if the signal indicates that the user does not desire to operate the powered assistive device, then minimal data, no data, a rest signal, or empty data packets are transmitted. In some embodiments, no data is transmitted until the user desires to activate the powered assistive device. In other embodiments, no data is transmitted in the resting state but an empty packet may be transmitted a "proof of life," "heart-beat," or "keep-alive" transmission on a minimum defined interval. For example, a code may be transmitted that acknowledges that the sensor is detecting a resting state. Schemes other than simple thresholding can be used to distinguish the rest state from the active state, including: discriminant analysis, support vector machines and machine learning.

In a non-limiting example, the sensor signal may be transmitted to the powered assistive device in a form of a transmitted signal, which is a digital signal having packets transmitted at intervals. A first transmission rate has a longer transmit interval and/or smaller packet size. The transmitted signal at the second rate has a smaller transmit interval and/or larger packet size. The longer transmit intervals and/or smaller packet sizes results in lower power consumption at the first rate, whereas the smaller transmit intervals and/or larger packet sizes result in comparatively more power consumption at the second rate. A ratio of the transmit intervals of the transmitted signal at the first rate to the second rate, in some examples, may be between 1.5:1 to 100:1, whereas a ratio of packet sizes of the transmitted signal at the first transmission rate to the second transmission rate, in some examples, may be between 1:2 to 1:1000. For example, the second rate may have a transmission interval of 10 ms while the first rate has an interval of 20 ms, giving a ratio of 2:1. The transmission intervals may be chosen such that at the second rate smooth control of the device is provided while at the first rate significant power savings are realized. As used herein, a significant power savings may be 50% or more in some examples. A ratio of the EMG signal of the user's muscle in the rest state to the EMG signal indicating minimum active state, in some examples, may be between 1:2 to 1:5000. In a non-limiting example, the amplified EMG signal of below 500 mV indicates a resting state of the muscle and 500 mV or above indicates that the muscle is in an at least minimum active state.

According to certain embodiments of the present invention, a muscle rest state of the user is determined by monitoring EMG as a means to save electrical power, thus extending battery life. In a non-limiting example, a muscle can be at rest for minutes at a time and, during this period, a longer transmit interval between consecutive transmitted signals (e.g., 100-500 ms) is appropriate. The longer transmit interval results in significant power savings. When substantive muscle activation returns, the transmit interval can be immediately returned to a smaller transmit interval (e.g., 10-50 ms). It should be noted that the power saving results in longer duration between charges for the powered assistive device.

According to the present disclosure, a system for transmission of a transmitted signal for a powered assistive device based on a signal of a sensor, comprises: a powered assistive device; a sensor node having a wireless transmitter adapted for digitally transmitting a transmitted signal, the sensor node adapted for receiving a sensor signal from a sensor attached to a user and monitoring the sensor signal, the sensor signal indicative of a rest or active state of the user; and a master node having a controller and a wireless receiver for receiving the transmitted signal from the wireless transmitter, the master node adapted for processing the transmitted signal and communicating a control signal to the powered assistive device, the wireless transmitter adapted to transmit the transmitted signal at a first rate when the sensor signal is indicative of the rest state and to transmit the transmitted signal at a second rate when the sensor signal is indicative of the active state, the second rate being greater than the first rate.

In some embodiments, the sensor signal indicative of the rest state of the user comprises a signal at or below a threshold value and the sensor signal indicative of an active state of the user comprises a signal above the threshold value; or the sensor signal indicative of the rest state of the user comprises a rate of change that is at or below a threshold value and the sensor signal indicative of an active state of the user comprises a rate of change that is above the threshold value.

According to some embodiments of this disclosure, the sensor signal being at or below the threshold level is indicative of the intent of the user to keep the muscle is at rest and the sensor signal being above the threshold level is indicative of the intent of the user to keep the muscle active or to move the muscle. It should be noted that in alternate embodiments, the sensor signal being above the threshold level is indicative of the intent of the user to keep the muscle at rest and the sensor signal being at or below the threshold level is indicative of the intent of the user to keep the muscle is active or to move the muscle. A person skilled in the art would be able to make use of this invention and apply it to the alternate embodiments based on the following disclosure.

In other embodiments of the system, the wireless transmitter is adapted for transmitting the transmitted signal using a communication protocol selected from the group consisting of Bluetooth, Zigbee, Z-Wave, ANT/ANT+ and 6LowPAN. The sensor signal may comprise a biological or movement signal for body activity of the user and the sensor is selected from the group consisting of an electromyographic (EMG) sensor, an inertial measurement unit (IMU) sensor, a force sensitive resistor, a liner transducer, a switch, a pressure transducer, an accelerometer, a gravitometer, a magnetometer, a inclinometer, a temperature sensor and a button. In some embodiments, the second rate of the transmitted signal has a transmission interval that is lower than a transmission interval of the transmitted signal at the first rate; and/or the second rate has a transmission interval that varies in a range of 1 ms to 10,000 ms, 1 ms to 1000 ms, or 10 ms to 100 ms.

The second rate of the transmitted signal may have a packet size that is larger than a packet size of the transmitted signal at the first rate; and/or the packet size at the second rate may dynamically vary from 1 byte to 244 bytes. In some embodiments, the signal received from the sensor is an analog sensor signal and the sensor node further comprises an analog front end (AFE). In other embodiments, the analog front end (AFE) is adapted for signal conditioning of the analog sensor signal received from the sensor, wherein the signal conditioning comprises analog to digital conversion, gaining, thresholding, applying pattern recognition/ machine learning techniques and/or filtering of the analog sensor signal. The system of claim 1, wherein the controller is adapted for signal conditioning the transmitted signal received from the wireless transmitter of the sensor node, the signal conditioning including digital to analog conversion, thresholding, applying pattern recognition/machine learning techniques, and/or filtering of the transmitted signal.

The powered assistive device may be selected from a group consisting of a powered prosthetic, a powered orthotic, a wrist rotator, elbow, multi-articulating hand, 1-DoF hand, knee, ankle, a powered upper and lower limb orthotic, split hook, gripper and an exoskeleton.

In alternate embodiments of the system, the sensor signal received from the sensor is digital. In some systems, the second rate varies dynamically when the sensor signal is indicative of an active state and/or varies proportionally with respect to a strength of the sensor signal. The master node may further comprise a transceiver that is adapted for communicating to and from an external device, the external device being selected from the group consisting of a base station, smart phone, wearable computer, personal digital assistant and a tablet.

The present disclosure also includes a method of adjusting transmission rate of a transmitted signal for a powered assistive device based on a signal of a sensor, the method comprising the steps of: providing a system for control of the powered assistive device, the system having a master node and a sensor node, the sensor node comprising a wireless transmitter, and the master node comprising a controller and a wireless receiver; receiving and monitoring a sensor signal from a sensor attached to a user at the sensor node; digitally transmitting a transmitted signal from the wireless transmitter of the sensor node to the wireless receiver at a first rate when the sensor signal is indicative of a rest state; digitally transmitting the transmitted signal at a second rate when the sensor signal is indicative of an active state, the second rate being greater than the first rate; and receiving the transmitted signal at the wireless receiver of the master node for controlling the powered assistive device.

According to some method embodiments, the sensor signal indicative of the rest state of the user comprises a signal at or below a threshold value and the sensor signal indicative of an active state of the user comprises a signal above the threshold value; or the sensor signal indicative of the rest state of the user comprises a rate of change that is at or below a threshold value and the sensor signal indicative of an active state of the user comprises a rate of change that is above the threshold value. In other method embodiments, the second rate varies dynamically when the sensor signal is indicative of an active state and/or varies proportionally with respect to a strength of the sensor signal.

According to some methods, the second rate of the transmitted signal has a transmission interval that is lower than a transmission interval of the transmitted signal at the first rate; and/or the second rate has a transmission interval that varies in a range of 1 ms to 10,000 ms, 1 ms to 1000 ms, or 10 ms to 100 ms. In some embodiments, the second rate of the transmitted signal has a packet size that is larger than a packet size of the transmitted signal at the first rate. The packet size in the second rate, according to some embodiments, may dynamically vary from 1 byte to 244 bytes. In other embodiments, the second rate of the transmitted signal has a transmission interval that is selected from the group consisting of 10 millisecond (ms), 20 ms, 50 ms, 100 ms and 500 MS.

The present disclosure also discloses another system for transmission of a transmitted signal for a powered assistive device based on a signal of a sensor, comprising: a sensor node having a wireless transmitter adapted for digitally transmitting a transmitted signal, the sensor node adapted for receiving a sensor signal from a sensor attached to a user and monitoring the sensor signal, the sensor signal indicative of a rest or active state of the user; and a master node having a controller and a wireless receiver for receiving the transmitted signal from the wireless transmitter, the master node adapted for processing the transmitted signal and communicating a control signal to the powered assistive device, the wireless transmitter adapted to transmit the transmitted signal at a first rate when the sensor signal is indicative of the rest state and to transmit the transmitted signal at a second rate when the sensor signal is indicative of the active state, the second rate being greater than the first rate.

BRIEF DESCRIPTION OF THE DRAWINGS

The accompanying drawings, which are included to provide a further understanding of the invention and are incorporated in and constitute a part of this application, illustrate embodiment (s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts. In addition, although the terms used in the present invention are selected from generally known and used terms, some of the terms mentioned in the description of the present invention have been selected by the applicant at his or her discretion, the detailed meanings of which are described in relevant parts of the description herein. Furthermore, it is required that the present invention is understood, not simply by the actual terms used but by the meaning of each term lying within.

Figure 1A:
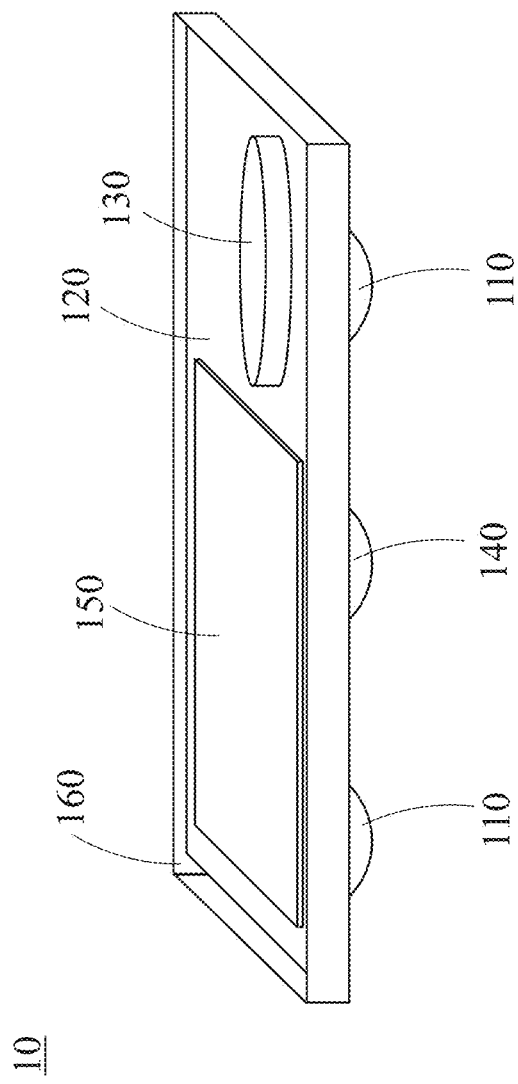
FIGS. 1A and 1B are perspective views of an exemplary sensor used in an embodiment of the system of the present disclosure.
Figure 1B:
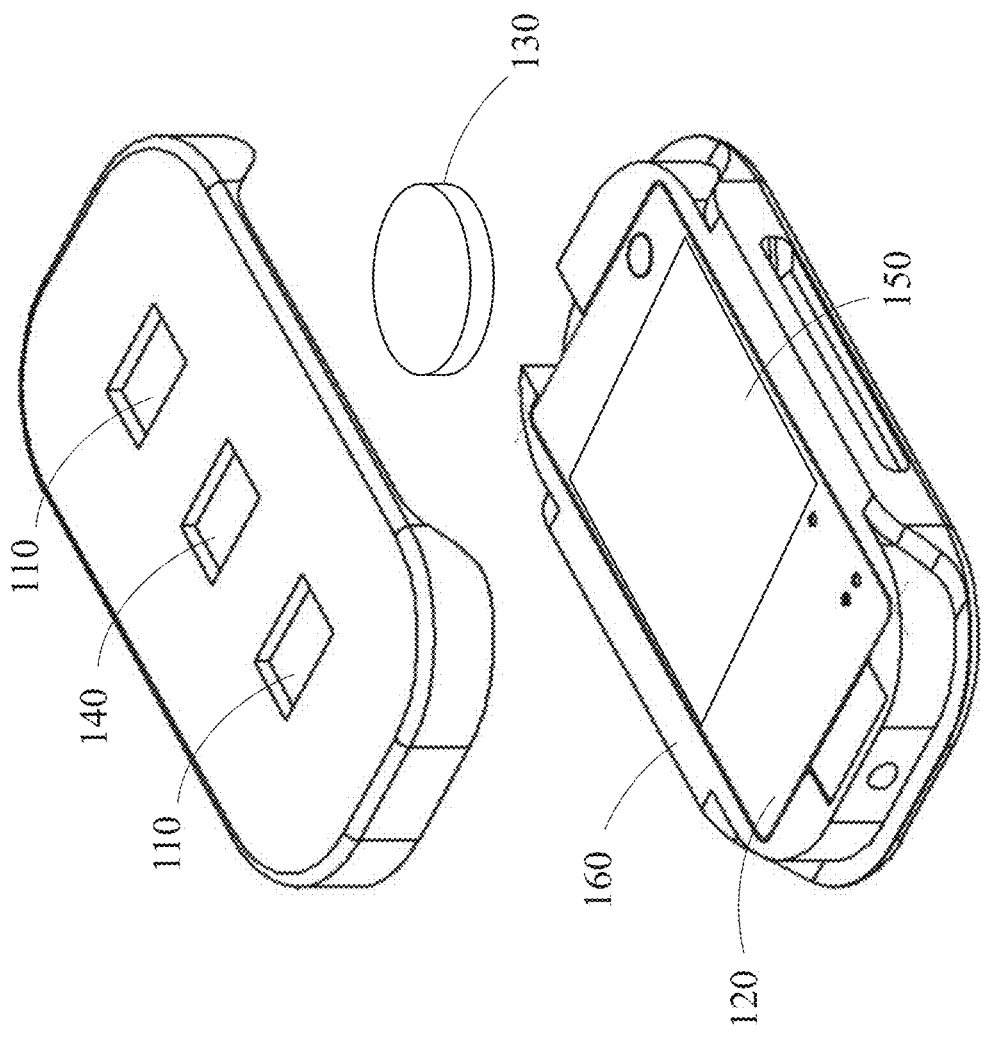

FIGS. 1A and 1B are perspective views of an exemplary sensor 10 used in an embodiment of the system according to the present disclosure. The components of the sensor 10 are placed on a circuit board 120. The circuit board 120 may have a rectangular, square, circular, elliptical or other suitable shape. Moreover, the circuit board 120 may be formed of a rigid, semi-rigid or flexible material. This embodiment is particularly focused on the acquisition of the EMG signals and thus the circuit board 120 has one reference electrode 140 and two active electrodes 110. the circuit board 120 may also contain a battery 130 and a transceiver 150. The sensor 10 is attached to a user (not shown) and, in one example, has a width of in a range of 10 to 40 mm. The sensor 10 may be enclosed in a case 160 for protection from the environmental elements. Non-limiting examples of the sensor 10 include a surface sensor and an intramuscular sensor. The signal from the surfaces of the active electrodes 110 is gathered with respect to the reference electrodes 140. In some embodiments, the reference electrodes 140 act as a ground for the gathered signal. In some embodiments, the reference electrodes 140 are placed far from the surfaces of the active electrodes 110, on an electrically neutral tissue of the user (not shown).

Figure 2:
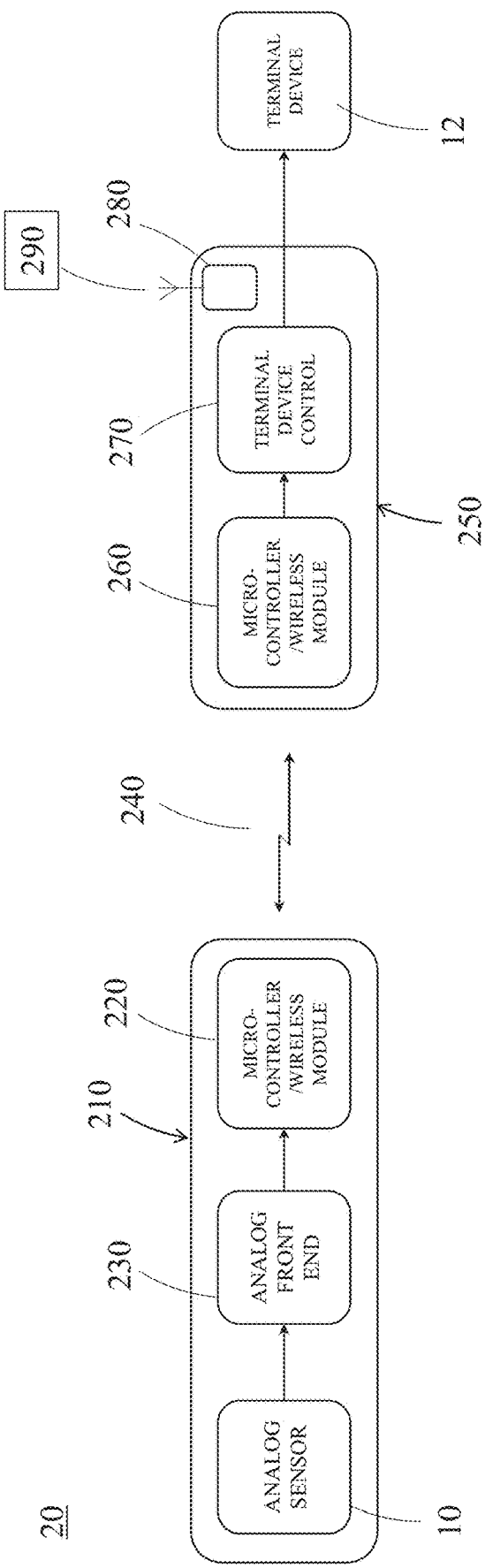
FIG. 2 is a block diagram of an embodiment of the present disclosure.

FIG. 2 is a block diagram of a system 20 for transmission of a transmitted signal according to the present disclosure. The system 20 includes a sensor node 210 that is interfacing to a sensor 10 and a master node 250 interfacing to a powered assistive device 12. The sensor node 210 includes a wireless module 220 having a transmitter for transmitting a transmitted signal 240 to the master node 250. The signal may be transmitted using Bluetooth Low Energy or any low power wireless communication protocol. The master node 250 includes a controller 270, such as a microcontroller or a microprocessor, which ultimately processes and/or passes the transmitted signal 240 to the powered assistive device 12 through signal conditioning such as digital to analog conversion and filtering, thresholding, etc., or directly without such conditioning. The master node 250 further includes a wireless receiver 260 for receiving the transmitted signal 240 from the wireless transmitter 220 of the sensor node 210 and may include a transceiver 280 for communicating to and from an external device 290. The external device 290 may be a base station, smart phone, wearable computer, personal digital assistant, a tablet or any other device to which communication is desired.

The sensor 10 may be an EMG electrode attached to the user's skin, an electromyographic (EMG) sensor, an inertial measurement unit (IMU) sensor, a force sensitive resistor, a liner transducer, a switch, a button or any other type of sensor suitable for a specific application. For an analog sensor 10 such as the EMG electrode, the sensor interface, i.e., the sensor node 210, may be an analog sensor node, which includes an analog front end (AFE) 230 for signal conditioning. In some embodiments, the signal from the sensor 10 is large enough that the analog front end 230 may not be required for signal conditioning and the raw sensor signal may be transmitted as the transmitted signal 240 from the sensor node 210 to the master node 250. The signal conditioning may include analog to digital conversion, and filtering, thresholding, etc. Examples of the powered assistive devices 12 include, but are not limited to, a multi-articulating hand, a wrist rotator or a powered orthosis. The analog sensor signal may be biological signals created by the user to demonstrate intent to move the powered assistive device such as EMG signals of a user or non-biological signals such as forces applied to a force sensitive resister (FSR), movement of an inertial measurement unit (IMU), etc.

The sensor signal, acquired from the sensor(s) 10, is transmitted, processed or unprocessed, via the sensor interface and moved into a processor memory. The raw or processed sensor signal 240, is then transmitted wirelessly over to the master (controller) node 250 which ultimately passes the sensor signal 240 through signal conditioning (digital to analog conversion, filtering, etc.) to a powered assistive device 12 (i.e. wrist rotator, multi-articulating hand, etc.) and/or to an external device 290 (e.g., smart phone or base station). Additional hardware components could be used to filter/smooth or otherwise process the output control. Additional control algorithms may be implemented on the master node 250 to control powered assistive devices 12. As noted above, other wireless protocols may also be used.

Figure 3:
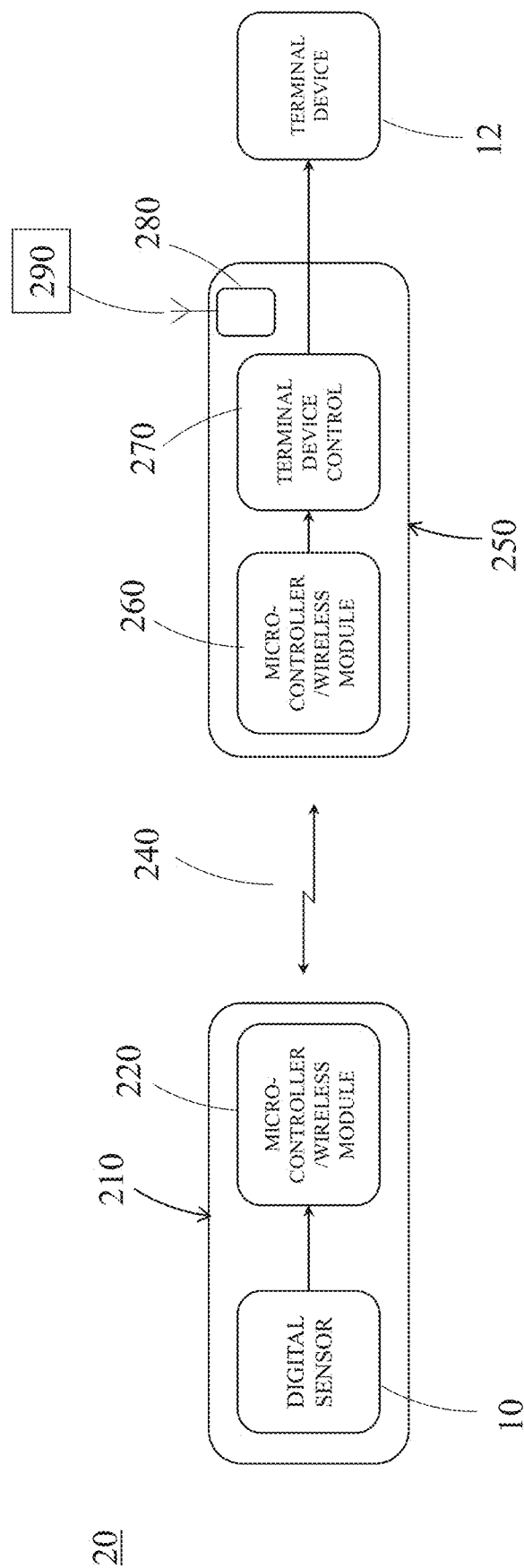
FIG. 3 is block diagram of another embodiment of the present disclosure.

FIG. 3 is a block diagram of another embodiment of a system 20 for transmission of a transmitted signal according to the present disclosure. The system 20 includes a sensor node 210 that is interfacing to a sensor 10 and a master node 250 interfacing to a powered assistive device 12. The sensor node 210 includes a wireless module 220 having a transmitter for transmitting a sensor/transmitted signal 240 to the master node 250. The signal may be transmitted using Bluetooth Low Energy or any low power wireless communication protocol. The master node 250 includes a controller 270, such as a microcontroller or a microprocessor, which ultimately processes and/or passes the sensor signal 240 to the powered assistive device 12 through signal conditioning such as digital analog conversion and filtering etc. The master node 250 may further include a wireless receiver 260 for receiving the transmitted signal 240 from the wireless transmitter 220 of the sensor node 210 and a transceiver 280 for communicating to and from an external device 290. The external device 290 may be a base station, smart phone, wearable computer, personal digital assistant, a tablet or other device.

The sensor 10 of FIG. 3 generates digital sensor signals. The sensor 10 generating digital signals may be digital versions of an inertial measurement unit (IMU) sensor, a force sensitive resistor, a liner transducer, a switch, a button, pressure transducer, accelerometer, gravitometer, magnetometer, inclinometer, temperature sensor or any other type of sensor suitable for a specific application. In some embodiments, a mechanomyogram (MMG) signal may be measured using an accelerometer or a microphone placed on the skin over the muscle. When measured using a microphone it may be termed as an acoustic myogram. Because the signal from the sensor 10 is digital, the sensor node 210 does not require an analog front device. Examples of the powered assistive devices 12 include, but are not limited to, a multi-articulating hand, a wrist rotator or a powered orthosis. In any embodiment of the present invention, a sensor described as analog may be replaced by a digital equivalent or a sensor described as digital may be replaced by an analog equivalent, where such equivalents are available, as will be clear to those of skill in the art. Further, in any embodiment, any other sensor type and sensor signal may be utilized that provides the necessary input for control. Sensors may also be combined. For example, an EMG sensor may be used in combination with a pressure sensor, with one or more of the sensors being used to determine the rest state and active state.

The sensor signal, acquired from the sensor(s) 10, is transmitted, processed or unprocessed, via the sensor interface and moved into a processor memory. The raw or processed sensor signal 240, is then transmitted wirelessly over to the master (controller) node 250 which ultimately passes the sensor/transmitted signal 240 through signal conditioning (digital to analog conversion, filtering, thresholding, etc.) to a powered assistive device 12 (i.e. wrist rotator, multi-articulating hand, etc.) and/or to an external device 290 (e.g., smart phone, base station, etc.). Additional hardware components could be used to filter/smooth or otherwise process the output control. Additional control algorithms may be implemented on the master node 250 to control powered assistive devices 12. As noted above, other wireless protocols may also be used.

Figure 4:
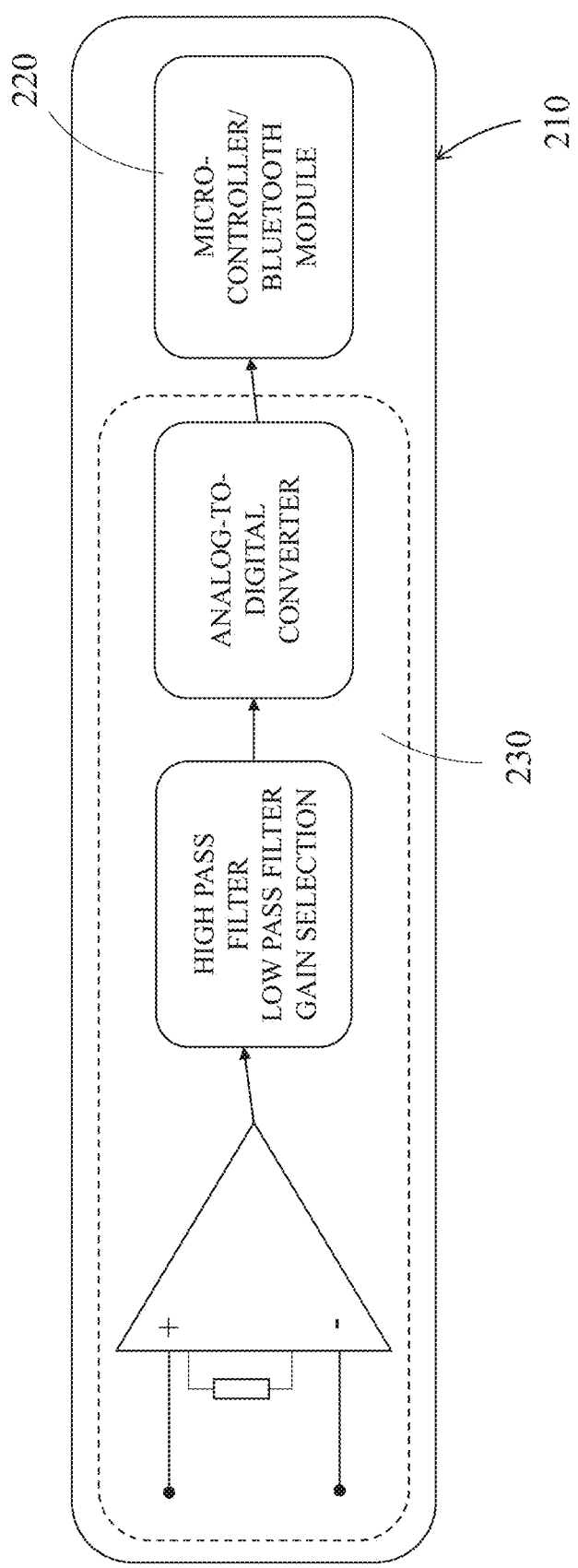
FIG. 4 is a block diagram of a sensor node of an embodiment of the present disclosure.

FIG. 4 is a block diagram of a sensor node 210 according to the present disclosure. The sensor node 210 consists of an analog front end 230 and a wireless module 220. The analog front end 230 has an instrumentation amplifier (e.g. AD8422), high pass filter (HPF), low pass filter (LPF), gain selector and a high resolution analog to digital converter. The sensor node 210 that is adapted to process analog sensor signals may be used in the system according to FIG. 2. It should be noted that other instrumentation amplifiers may also be used for other embodiments.

Figure 5:
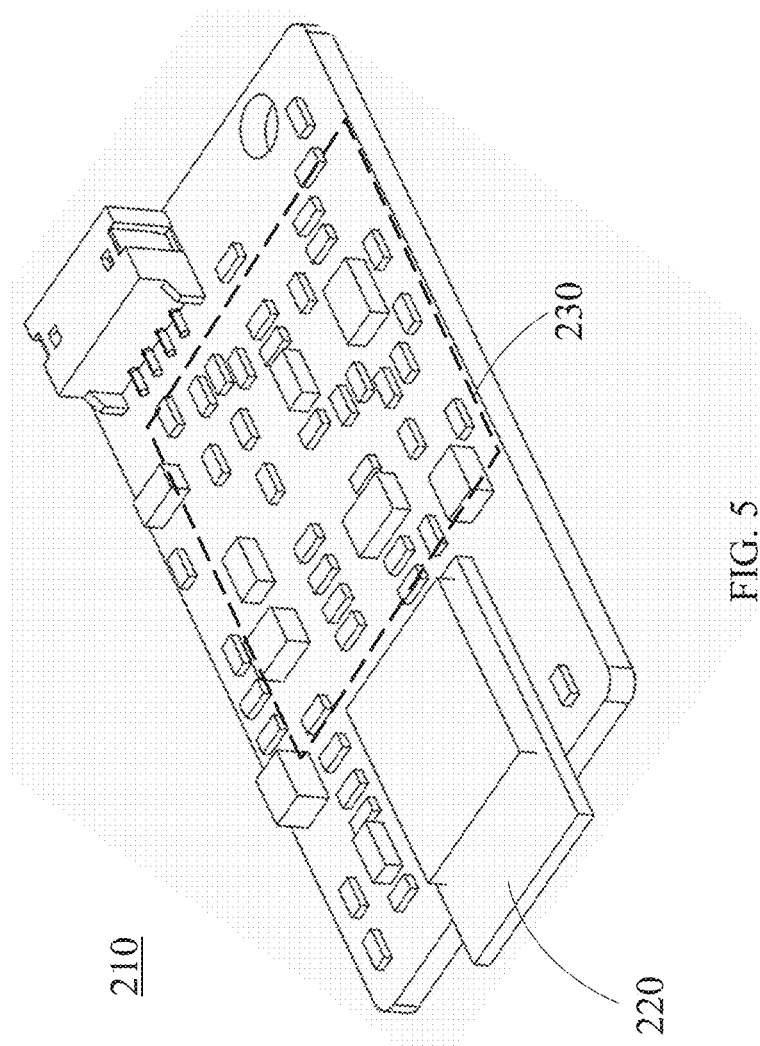
FIG. 5 is an image of the component(s) of an exemplary analog sensor node for FIG. 2.

FIG. 5 shows an image of the analog sensor node 210 that may be used in the system according to FIG. 2. In FIG. 5, the analog sensor node 210 consists of an analog front end 230 for receiving and monitoring a sensor signal from a sensor attached to a user and a transmitter 220 that is adapted for digitally transmitting a transmitted signal. The sensor is generating an analog signal.

A powered assistive device is not actuated for much of the time during which it is worn. During this time when the muscle is at rest, a longer transmit interval between consecutive signals (e.g., 100-500 ms) is appropriate, resulting in significant power savings.

An embodiment of the system of the present invention uses a variable transmission rate which translates into varying transmission intervals. During periods when the EMG/sensor activity is below a usable threshold, meaning little or no EMG/sensor activity, the transmission rate is reduced and the interval between transmits is increased. There are several ways of monitoring EMG/sensor activity in the user depending on the embodiment and/or user. The embodiments described herein use the EMG signal as an example. "EMG activity" is commonly defined as the standard deviation of the EMG signal. Other indicators of "activity" are also common, including the number of zero crossings experienced by the EMG signal, the number of slope sign changes experienced by the EMG signal and the signal length (sum of the absolute difference between adjacent EMG signal samples). During periods when EMG activity is above a threshold where it would be used for control, the transmission rate is increased and the interval between transmits is reduced. Potentially, a minimum transmission rate is defined to be used to keep the connection "alive".

In addition to variable transmission rates, sending a signal with smaller (or empty) packets when the arm is at rest could benefit power savings. For example, a single "no activity" code can be transmitted or EMG activity that has been processed and then the sampling rate could be decimated in time. A smaller amount of sensor data results in the transmission of a smaller wireless packet (fewer transmitted bytes), reducing sensor electrical power consumption.

Even if a prosthetic device is not actuated for most of the time during which it is worn, the EMG signal is not zero-valued when a muscle is at rest. Rather, a small noise signal exists due to residual bioelectrical activity within the body, electrode-skin interface noise, power-line interference and noise in the EMG analog front end. If left unaccounted for, an EMG-controlled device would "drift" from its intended rest position due to inadvertent, low-intensity action attributed to this noise. For this reason, commercial myoelectric controls implement a dead band to the processed EMG, essentially ignoring this low-intensity noise.

In the present invention, the muscle rest state may be continuously monitored in the sensor nodes, as a means to save electrical power, thus extending battery life of the device. This can also apply to other sensors aside from EMG (e.g. IMU activity below a threshold or within a dead-band, switch input state not changing, force sensitive resistance below threshold/within dead-band, etc.). As will be described herein below with respect to test results from testing on a prototype, if transmit intervals are extended to 100 ms, then significant power savings are realized. This interval is too long during ideal active myoelectric control and would negatively impact prosthesis performance. However, a muscle can be at rest for minutes at a time. During this period, the longer transmit interval is appropriate. When substantive muscle activation returns, the transmit interval can be immediately returned to a more appropriate value (e.g., 10-50 ms).

Some embodiments of the present invention focus on a dynamic interval adjustment and/or a dynamic packet size to find the minimal impact on battery life while still balancing performance requirements. This can apply to a single sensor 10 or multiple sensors 10 of varying type. The modes may include (a) a two-state active/sleep cycle, (b) a varying transmission interval (where the movement or EMG activity level dictates transmission interval), (c) a varying packet size (where the movement of EMG activity level dictates packet size) and (d) a sensor dependent transmission. The two-state mode would toggle sensor nodes 210 between inactive and active modes. The wake mode might be activated for all sensor nodes 210 when one sensor node is woken up. The varying transmission interval mode would work similarly to the two-state mode but be dependent on the most active sensor node's 210 activity. In this mode, all sensor nodes 210 would sleep until activity is observed. At this point all sensor nodes 210 would be woken from sleep to report. Finally, the sensor dependent transmission mode would be determined on a node-by-node basis, such that each individual sensor 10 would report based only on its own activity, independent of each other sensor 10. The minimum reporting interval for each sensor node 210 would be determined such that performance specifications will be met.

It is observed that during inactivity, transmitting at intervals of 500 ms or longer may not substantially alter wireless module power consumption compared to not transmitting at all. The remaining circuitry (analog/digital front end, wireless Module microprocessor) remains fully active during this time, constantly acquiring data to determine the need to wake from rest processing. Hence, it is likely that each "resting" node should communicate with the master using a predefined minimum interval (e.g. ~300 ms). A longer interval is acceptable, if an empty packet is transmitted or if processed (and decimated) data are transmitted.

There are several advantages to retaining these infrequent transmissions, even if only an empty packet or decimated data are transmitted. First, there is no discernible loss in battery life of the device when transmitting at such long intervals (compared to not transmitting at all when a muscle is inactive). Second, the master node 250 is provided a "proof of life," "heart-beat," or "keep-alive" transmission on a minimum defined interval. This would allow the master node 250 to notify the end user of lost communication with the sensor nodes 210. Third, this transmission can be used to transfer information (e.g. configuration updates, battery or sensor status, etc.) between the sensor nodes 210 and master nodes 250 as well as be used for synchronization timing between nodes. Fourth, for certain sensors and sampling rates, the raw data can fit into a packet that is transmitted at this interval, thus reducing message overhead and improving data payload. When the size of the packet has no discernable role in electrical power consumption, the master node 250 might as well benefit from receiving the raw data samples during rest.

The test conditions and test results of a preliminary EMG analog sensor node prototype are described below.

Specifics of Prototype Test Setup

FIG. 5 shows a preliminary EMG sensor node 210 prototype. The dashed area is a prototype EMG Analog front end 230. On the bottom is a TI CC2640R2 BLE Module 220. The Analog Front End (AFE) 230 consists of an instrumentation amplifier and a passive band-pass filter and DC level-shifter. The Master Node includes a TI CC2640R2 Launch Pad (not shown).

Baseline Conditions

Analog Front End (AFE) baseline current for the prototype is 0.8-0.9 mA (drawn from 3.3 V power supply).

Test Conditions

Test conditions varied over a set of variables (fixed within each test) including:
  Transmission intervals (10 ms, 20 ms, 50 ms, 100 ms)
  Transmit powers (+0 dB, +5 dB)
  ADC sampling rates (1000 Hz, 2000 Hz, 4000 Hz)
  Transmission modes ((a)—Raw, (b)—Processed and decimated EMG, (c)—Raw with processing, (d)—One byte/interval)

(a) Only the "raw" EMG samples (two-byte, integer) were transmitted, and EMG processing was not used. This condition operates the wireless EMG node as a simple data collection sensor.

(b) EMG processing was enabled, and only one four-byte float was transmitted per interval. This condition greatly reduced the bandwidth of transmitted information by processing the EMG signal on-board the wireless node.

(c) Only the "raw" EMG samples were transmitted, and EMG processing was enabled. This condition mimicked rest detection during periods when the muscle activity was not at rest (the EMG signal still needed to be transmitted).

(d) EMG processing was enabled, and only one byte was transmitted per interval. This condition mimicked the detection of a "rest" interval, during which no data need be transmitted. (One byte was transmitted, which is the minimum packet size currently available.)

Test Results

Figure 6:
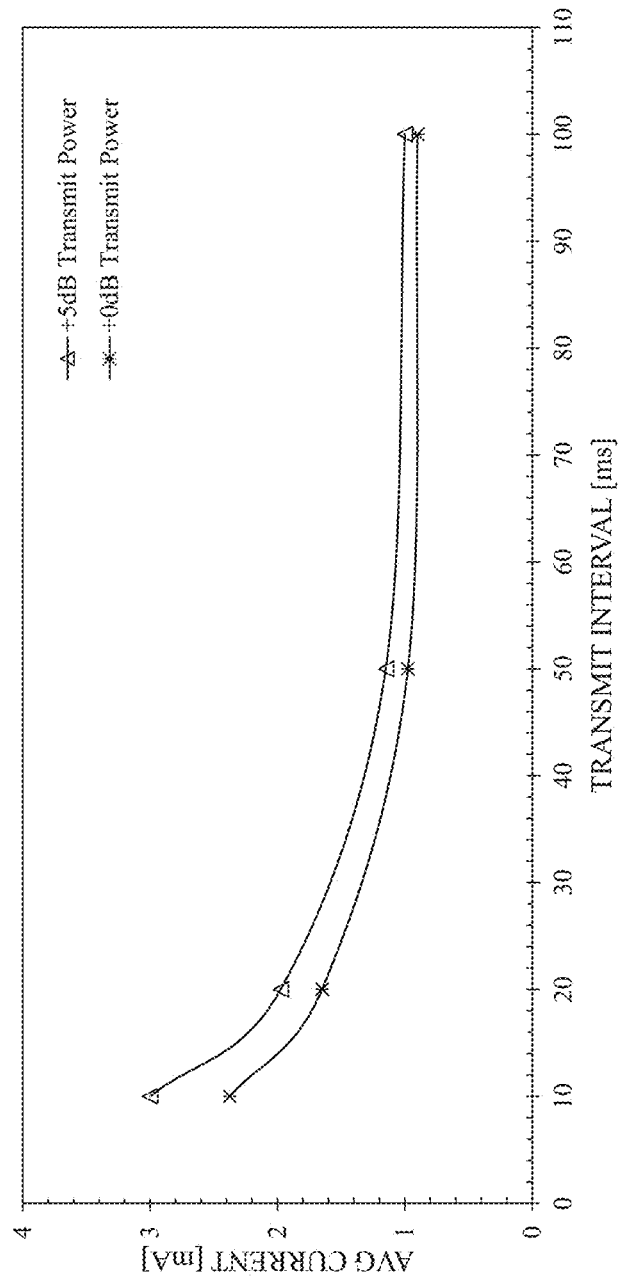
FIG. 6 is a graph of average current verses transmission interval for a transmitted signal from a wireless transmitter.

Results from testing are provided in Table I and the graph in FIG. 6.

Observations/Conclusions

1. No major variations observed between modes (raw, one byte).

TABLE I

Current consumption (mA) of the TI CC2640R2 BLE Module
(excludes analog front end current)

| | Raw Signal $F_{Sample}$ (Hz) | | | One Byte/Interval $F_{Sample}$ (Hz) | | |
|---|---|---|---|---|---|---|
| Interval | 1000 | 2000 | 4000 | 1000 | 2000 | 4000 |
| Transmit Power = +5 dBm (Maximum) | | | | | | |
| 10 ms | 3.0 | 3.0 | 3.1 | 3.0 | 3.0 | 3.0 |
| 20 ms | 1.9 | 1.9 | 1.9 | 1.9 | 1.9 | 1.9 |
| 50 ms | 1.2 | 1.2 | NA | 1.2 | 1.2 | 1.3 |
| 100 ms | 1.0 | NA | NA | 1.0 | 1.1 | 1.0 |
| Transmit Power = +0 dBm (Minimum) | | | | | | |
| 10 ms | 2.3 | 2.4 | 2.4 | 2.3 | 2.4 | 2.3 |
| 20 ms | 1.6 | 1.6 | 1.6 | 1.7 | 1.7 | 1.8 |
| 50 ms | 1.0 | 1.0 | NA | 1.0 | 0.9 | 1.0 |
| 100 ms | 0.9 | NA | NA | 0.9 | NA | NA |

NA = denotes packet size too large or unreliable transmission

2. No major variations observed at different ADC Sample rates (1000, 2000 or 4000 Hz).

3. Transmission interval has largest impact on power savings
  a. >50 ms interval no additional (significant) power savings
  b. <50 ms interval increases average power draw 4. Data payload (packet size) no significant change in current consumption (i.e., Raw packets from varied ADC conversion rates).

5. Increasing the transmission interval reduces average current draw (i.e. from 10 ms to 100 ms).

6. Transmit power setting (+0 dB vs+5 dB) has a modest offset on overall current draw, with the magnitude of the effect growing larger with increasing transmission frequencies.

Figure 7:
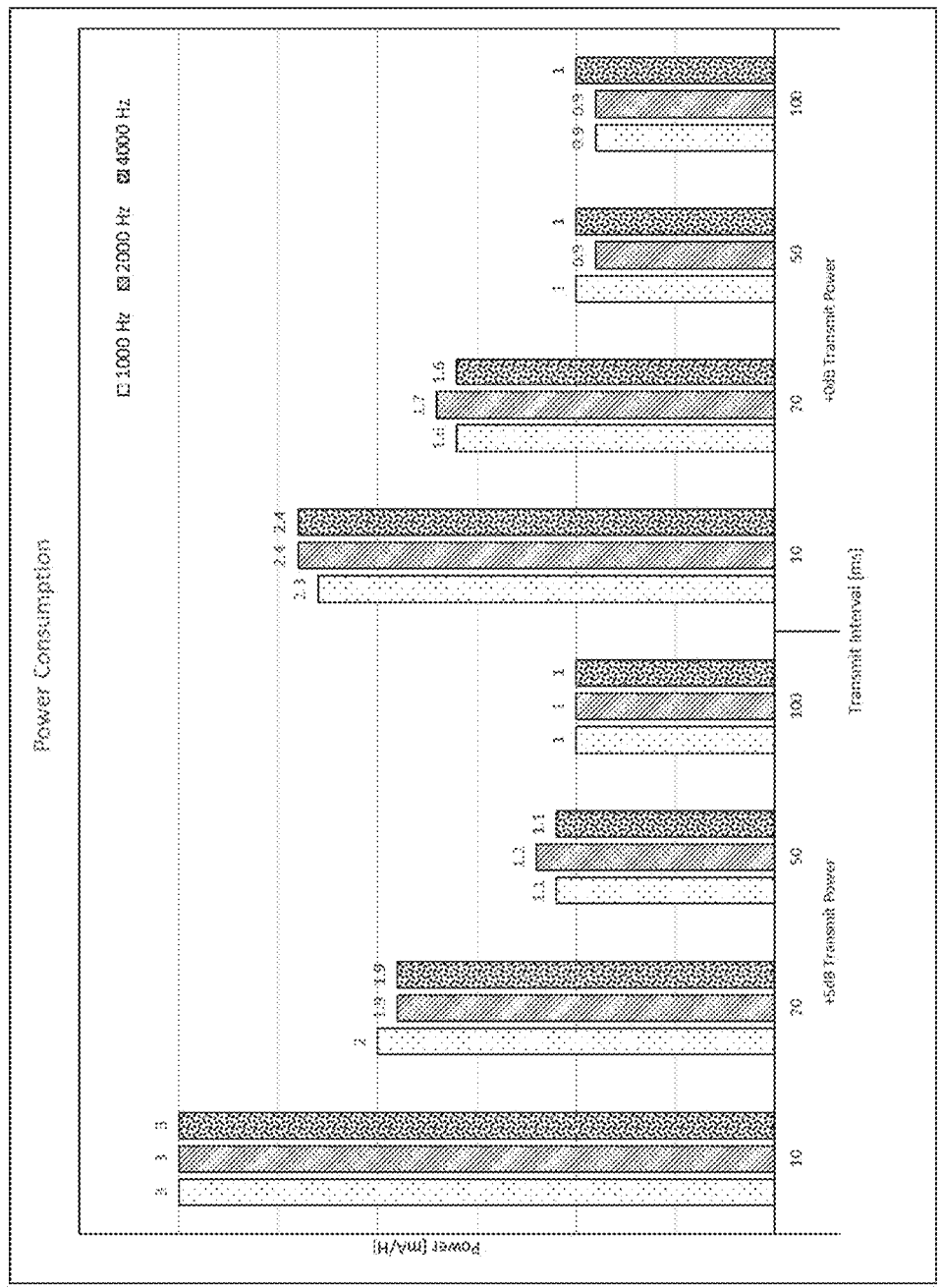
FIG. 7 is a graph of power consumption verses transmission interval for various frequencies of the transmitted signals.

FIG. 7 is a detailed graph based on Table 1 showing power consumption between different transmit intervals and transmit power. For example, the power consumption at the transmission interval of 10 ms was about 3 mA/H when the signal was transmitted at 1000, 2000 and 4000 Hz. In other words, the power consumption did not changed for these frequencies. Results for other transmission intervals are also shown in the FIG. 7.

Figure 8:
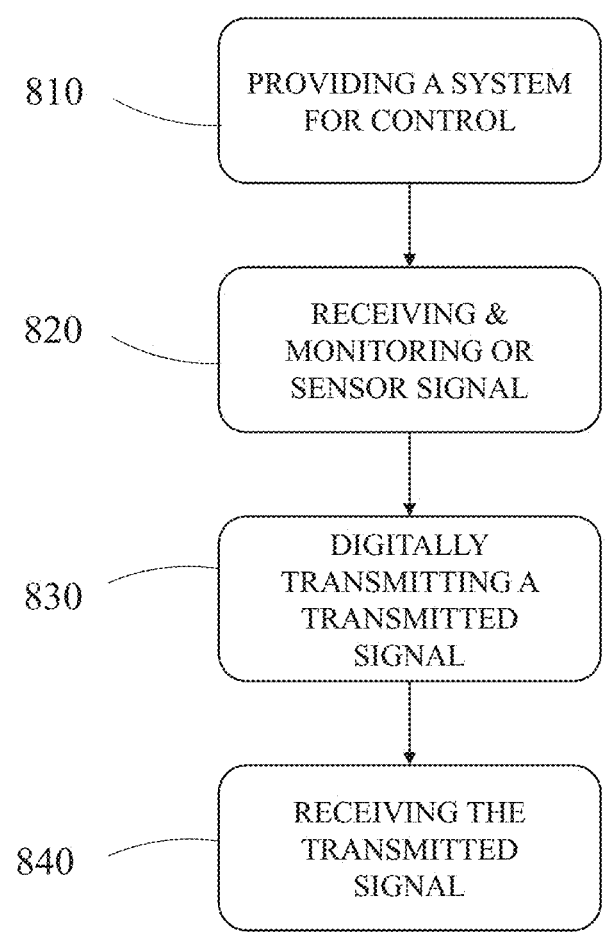
FIG. 8 is a block diagram of a method of adjusting transmission rate according to the present disclosure.

FIG. 8 is a block diagram of a method 800 of adjusting transmission rate of a transmitted signal for a powered assistive device based on a signal of a sensor. A system is provided at 810 for control of the powered assistive device. The system has a master node and a sensor node that are discussed in detail above. The sensor node has a wireless transmitter, and the master node has a controller and a wireless receiver. At 820, a sensor signal is received from a sensor attached to a user and is monitored at the sensor node. At 830, a transmitted signal is digitally transmitted from the wireless transmitter of the sensor node to the wireless receiver at a first rate when the sensor signal is at or below a threshold value. The transmitted signal is also digitally transmitted at a second rate when the sensor signal is above the threshold value. At 840, the transmitted signal is received at the wireless receiver of the master node for controlling the powered assistive device.

In some embodiments of the method 800, the second rate varies dynamically when the sensor data is above the threshold value. In other embodiments, the second rate of the transmitted signal has a transmission interval that is lower than a transmission interval of the first rate and the transmission interval of the second rate is selected from the group consisting of 10 millisecond (ms), 20 ms, 50 ms, 100 ms and 500 ms.

The present invention has been described with reference to some embodiments. However, it is realized that variants and equivalents to the preferred embodiments may be provided without departing from the scope of the invention as defined in the accompanying claims. It is to be understood that both the foregoing general description and the detailed description of the present invention are exemplary and explanatory and are intended to provide further explanation of the invention as claimed. It is not intended to be exhaustive or to limit embodiments to the precise form disclosed. It is the following claims, including all equivalents, which define the scope of the invention.

The invention claimed is:

1. A method of power saving for a powered assistive device controlled by a sensor attached to a user communicating wirelessly with the powered assistive device, the method comprising the steps of:
  receiving a sensor signal via the sensor attached to the user, the sensor signal indicative of a state of the user including at least a rest state and an active state;

determining the state of user based on the sensor signal; and wirelessly transmitting a communication signal at a transmission rate for controlling the powered assistive device;

wherein the transmission rate is at a first rate when the state of the user is the rest state and at a second rate when the state of the user is the active state, the second rate being greater than the first rate.

2. The method claim 1, further comprising:

converting the communication signal into a control signal; and controlling the powered assistive device using the control signal.

3. The method of claim 1, wherein:

the sensor signal indicative of the rest state of the user comprises a signal at or below a threshold value and the sensor signal indicative of the active state of the user comprises a signal above the threshold value; or the sensor signal indicative of the rest state of the user comprises a rate of change that is at or below a threshold value and the sensor signal indicative of the active state of the user comprises a rate of change that is above the threshold value.

4. The method of claim 1, further comprising varying the second rate dynamically when the sensor signal is indicative of the active state and/or varying the second rate proportionally with respect to a strength of the sensor signal.

5. The method of claim 1, wherein:

the second rate has a transmission interval that is lower than a transmission interval at the first rate; and/or the second rate has a transmission interval that varies in a range of 1 ms to 10,000 ms, 1 ms to 1000 ms, or 10 ms to 100 ms.

6. The method of claim 1, wherein the powered assistive device is selected from a group consisting of a powered prosthetic, a powered orthotic, a wrist rotator, elbow, multi-articulating hand, 1-DoF hand, knee, ankle, a powered upper and lower limb orthotic, split hook, gripper and an exoskeleton.

7. The method of claim 1, wherein the second rate of the communication signal has a packet size that is larger than a packet size of the communication signal at the first rate; and/or the packet size at the second rate dynamically varies from 1 byte to 244 bytes.

8. The method of claim 1, wherein the sensor signal comprises a biological or movement signal for body activity of the user and the sensor is selected from the group consisting of an electromyographic (EMG) sensor, an inertial measurement unit (IMU) sensor, a force sensitive resistor, a liner transducer, a switch, a pressure transducer, an accelerometer, a gravitometer, a magnetometer, a inclinometer, a temperature sensor and a button.

9. The method of claim 1, further comprising signal conditioning the sensor signal, the signal conditioning comprising analog to digital conversion, gaining, thresholding, applying pattern recognition/machine learning techniques and/or filtering of the analog sensor signal.

10. The method of claim 1, further comprising signal conditioning the communication signal, the signal conditioning including digital to analog conversion, thresholding, applying pattern recognition/machine learning techniques, and/or filtering of the transmitted signal.

11. The method of claim 1, further comprising communicating to and from an external device, the external device being selected from the group consisting of a base station, smart phone, wearable computer, personal digital assistant and a tablet.

* * * * *